United States Patent [19]

Goupil

[11] Patent Number: 4,699,781

[45] Date of Patent: Oct. 13, 1987

[54] SUN PRODUCTS

[76] Inventor: Jean-Jacques Goupil, 30 Avenue du Président Wilson, 94230 Cachan, France

[21] Appl. No.: 21,604

[22] Filed: Mar. 2, 1987

Related U.S. Application Data

[63] Continuation of Ser. No. 858,863, Apr. 30, 1986, abandoned, which is a continuation of Ser. No. 374,189, May 3, 1982, abandoned, which is a continuation of Ser. No. 101,506, Dec. 10, 1979, abandoned, which is a continuation of Ser. No. 821,092, Aug. 2, 1977, abandoned.

[30] Foreign Application Priority Data

Aug. 4, 1976 [FR] France ................ 76 23799

[51] Int. Cl.$^4$ .............. A61K 7/42; A61K 7/44
[52] U.S. Cl. ................ 424/59; 424/60; 514/873
[58] Field of Search ................ 424/59, 60

[56] References Cited

FOREIGN PATENT DOCUMENTS 2004142  3/1969  France ................ 424/332

OTHER PUBLICATIONS

Sagarin, 5/1975, vol. I, 2nd ed., p. 297.
Bennett, The Cosm. Formulary, 1937, p. 83.
Finnemore, 7/1932, Essential Oils, p. 413.
Chem. Abs., 1956, vol. 50, p. 12037.
Chem. Abs., 1937, vol. 31, p. 3911.
Chem. Abs., 1937, vol. 31, p. 3475.
Chem. Abs., 1937, vol. 31, p. 3030.
Chem. Abs., 1970, vol. 73, p. 28988.
Späth et al., Chem Abs., 1934, pp. 1683, 1684, vol. 28.
Okahara, Chem. Abs., 1936, vol. 30, pp. 7575.
Merz et al., Chem. Abs., 1936, vol. 30, p. 7113.
Franke, Chem. Abs., 1912, vol. 6, pp. 492 & 493.
Thoms et al., Chem. Ber., 1912, Jahr. 45, pp. 3705–3712 (Corres. Chem. Abs, vol. 7, p. 1191).
Journ. Invest. Dermatology, 1959, vol. 33.
Markland, Cosmetics & Toiletries, 3/1976, vol. 91, pp. 79 to 81.

*Primary Examiner*—Dale R. Ore
*Attorney, Agent, or Firm*—Darby & Darby

[57] ABSTRACT

Sun product based on natural bergamot essence which contains between about 2.75 mmg and about 27.50 mmg of 5-methoxy psoralene or bergaptene per 100 g of sun product, an ultra-violet B filter, all incorporated in a suitable oily excipient.

9 Claims, No Drawings

SUN PRODUCTS

This is a continuation of application Ser. No. 858,863, filed 4/30/86 in turn a continuation of Ser. No. 374,189 filed May 3, 1982, in turn a continuation of Ser. No. 101,506, filed Dec. 10, 1979, and in turn a continuation of Ser. No. 821,092, filed Aug. 2, 1977, all now abandoned.

The present invention relates to sun products based on bergamot essence.

It is known that natural "sun-tanning" is a result of the action of the ultra-violet rays on the melanocytes of the human skin, these melanocytes being the specific cells on the periphery of the dermis which are responsible for melanogensis.

Melanocytes are capable of accumulating granules of melamin or melanosomes. When the melanocyte is in the natural state it liberates the melanosomes into the epidermis where they are picked up by other cells, known as keratimocytes which accumulate them.

Transfer is carried out by types of cellular extensions known as dendrites.

A natural sun filter which protects the skin and which forms a barrier to the action of the harmful ultra-violet rays is obtained.

When a suitable composition containing natural bergamot is spread on the skin, the action of the rays of sun are augmented by the action of the essential oil of natural bergamot and an initiation and increase in the speed and intensity of melanogenesis is observed. The so-called "sun-tanning" products containing natural bergamot essence are therefore valuable in that they allow a reduction in the period of exposure to the sun required for obtaining good natural protection of the skin from the sun by sun-tanning.

However, an excess in the proportion of natural bergamot essence in the sun-tanning product is likely to produce effects which are bad for the skin, since in excess it combines with the ultra-violet rays of the sun. This is the reason why in known products the precaution of remaining below very low limits when composing sun-tanning products containing natural bergamot essences is observed.

These very low limits are observed in practice because compositions based on hydro-alcoholic excipients are considred likely to endanger the skin if a content of pure natural bergamot essence of about 0.60% by weight of the considered product is used.

Whatever excipient is used, even if it is an oily excipient, the sun-tanning products manufactured at the present never exceed the maximum of 0.60 g% of natural essence of pure bergamot in their compositions.

These limiting proportions, are justified because of the fact that the main active ingrediennt with regard to the photo-dynamic content in the pure natural essence of bergamot is 5-methoxy psoralene, also known as "bergaptene" and the fact that the product contains varying amounts of this essence depending not only upon the soil, the climate and the meteorological conditions but also to a significant degree depending upon the harvesting season.

The bergaptene content in a bergamot essence may be measured accurately by gas chromatography. I have determined that it is possible to use higher proportions of pure natural bergamot essence than used hitherto in reasonable conditions and without danger.

Firstly, in order to determine the proportions of bergaptene which could be safely introduced into sun compositions, systematic sun-tanning tests were carried out on groups of twenty people having skins of types I, II, III and IV. It is known that dermatologists have determined four types of skin, the type I skins which do not tan and which burn, in other words those which are very prone to solar erythema, the type II skins which tan with difficulty and are prone to solar erythema, the type III skins which tan easily and are hardly prone to solar erythema and the type IV skins which tan perfectly and without problems.

The results obtained are set out in the Table and show that erythema does not occur in doses of up to 20 mmg of bergaptene per 100 g composition on any skin type and that the period required for obtaining an optimum sun-tan is shorter, the higher the bergaptene content in the composition.

| Bergaptene in mmg per 100 g of sun composition with oily exipient | Type II Skin Period of Exposure (in hours) for obtaining optimum sun-tan | | Erythema all skins |
|---|---|---|---|
| | with Bergaptene | without Bergaptene | |
| 3 mmg | 12 hours | 24 h in 6 days | none |
| 5 mmg | 10 hours | 24 h in 6 days | none |
| 10 mmg | 9 hours | 24 h in 6 days | none |
| 15 mmg | 8 hours | 24 h in 6 days | none |
| 20 mmg | 7 hours | 24 h in 6 days | none |
| 25 mmg | 6 hours | 24 h in 6 days | 1 case/20 skins type I |
| 30 mmg | 5 hours | 24 h in 6 days | 8 cases/20 skins type I<br>4 cases/20 skins type I |

The results of these tests enabled us to determine a new upper limit for the bergaptene content (that is 5-methoxy psoralene) of a sun composition with oily excipient. This upper limit is about 27.5 mmg of bergaptene per 100 g of sun composition with oily excipient.

Accordingly the present invention provides a sun product which comprises 5-methoxy psoralene or bergaptene in an amount of up to 27.50 mmg per 100 gm of sun product, an ultra-violet B filter and an oily excipient.

The lower limit varies as a function of the desired effectiveness but maybe fixed at 2.75 mmg of bergaptene per 100 g of sun composition with oily excipient in order to obtain a much more rapid "sun-tanning" effect than that known in the past.

The quantity B of bergaptene to be introduced into 100 g of sun composition in order to obtain an accelerated sun-tanning effect without the risk of solar erythema is generally between 2.75 mmg and 27.5 mmg.

If $\alpha$ is considered as the bergaptene content in the pure natural bergamot essence, the proportion E of this essence to be introduced into 100 g of composition is $E = B/\alpha$ and is therefore between $2.75/\alpha$ mmg and $27.5/\alpha$ mmg.

The bergaptene content in the different pure natural bergamot essences used has been carefully determined by gas chromotagraphy and may vary between 1 per 1000 and 5 per 1000.

It follows from this data that the maximum quantity of pure natural bergamot essence that can be introduced into 100 g of sum composition should vary between 5.5 g (B=27.5 mmg and α=5%) and 27.5 g (B=27.5 mmg and α=1%).

In reality that much pure natural bergamot essence is never introduced into a sun product and the maximum dosage reached is generally 3 g of pure natural bergamot essence in 100 g of sun product; that is a dosage of 3%.

This is because on the one hand the optimum perfume of the sun product is obtained with 2 to 3% bergamot essence and on the other hand a dosage of more than 3% of natural essence can not be tolerated by certain skins.

For a bergamot essence containing 4% of bergaptene, the introduction of 3% of this essence into a sun product, corresponds to an addition of 12 mmg of bergaptene per 100 g of sun product. If the sun-tanning properties of the product are to be accelerated and to attain the maximum content of 27.5 mmg of bergaptene per 100 g of product, the complementary quantity of 5-methoxy psoralene or pure bergaptene is added to the pure natural bergamot essence, that is in the present case 15.5 mmg.

The sun products of the present invention are quite remarkable because of their high bergaptene content: maximum limit of 27.5 mmg of bergaptene per 100 g of sun product instead of 2.5 mmg in the former products, in other words an upper limit multiplied by about 10. The higher bergaptene content can be attained by introducing pure natural bergamot essence preferably to a maximum of 3%, and by adding the desired complementary quantity of pure bergaptene.

The preferred amounts of bergaptene are from 5 to 20 mmg per 100 g of composition.

The pure natural bergamot essences which are preferably used for carrying out the invention have bergaptene contents of 4%.

The excipients used for the sun products of the invention are oily excipients, with the exclusion of aqueous excipients, emulsions with continuous aqueous phase and particularly hydro-alcoholic excipients. Vegetable or mineral oils maybe used for obtaining liquid sun-tanning products or lanolins and other oily substances of animal or mineral origin maybe used for obtaining creams.

As examples of oily excipients, it may be cited peanut oil, Turnsole oil, coco-nut oil, liquid paraffin, lanoline, stearin, spermaceti, saturated fatty acids triglycerids from $C_8$ to $C_{12}$.

Furthermore, the compositions must contain substances acting as ultra-violet B filters such as for example ethyl hexyl paramethoxy cinnamate and 3-(4-methylbenzylidene)-Camphor. The proportions of these substances should preferably not be below 1.5% of ethyl hexyl paramethoxy cinnamate, which screens radiation of between 2600 A and 3,400 A and 1% of 3-(4-methylbenzylidene)-Camphor which screens radiation having wavelengths between 2200 A and 3150 A. The maximum contents for each of these two filters are preferably 4%. It is understood that the two above-mentioned substances are quoted as an example of suitable ultra-violet B filters and they may be replaced by similar substances producing equivalent effects, such as paraaminobenzoic (P.A.B.A.) and paramethoxy cinnamic acid diethanolamine.

The composition may also contain other substances which are beneficial to the skin such as vitamins or substances which form an additional screen.

The following Examples illustrate the present invention.

EXAMPLE 1

A sun-tanning product was prepared composed as follows, per 100 f of total composition:
Bergaptene: 0.0075 grammes
Ethyl hexyl paramethoxy cinnamate: 2,0000 grammes
3-(4-methylbenzylidene)-Camphor: 1,0000 grammes
Oily excipient based on isopropyl myristate and vegetable and mineral oils: quantity required for 100%

EXAMPLE 2

A sun-tanning product was prepared composed as follows, per 100 g of total composition:
4% pure natural bergamot essence: 3 grammes (Bergaptene equivalent: 0.012 g)
Pure bergaptene: 0.003 grammes
Ethyl hexyl paramethoxy cinnamate: 3 grammes
3-(4-methylbenzylidene)-Camphor: 1 gramme

What is claimed is:

1. A sun tanning product consisting essentially of from 2.75 to about 27.5 mmg of 5-methoxypsoralen per 100 gm of said product, an ultraviolet B-filter and an oily excipient.

2. A sun tanning product according to claim 1, wherein said ultraviolet-B-filter comprises at least about 1.5% by weight of said product of ethylhexyl paramethoxy cinnamate.

3. A sun tanning product according to claim 1 further comprising about 1% by weight of 3-(4-methylbenzylidene)-Camphor.

4. A sun tanning product according to claim 1, comprising per 100 g of sun product based on an oily excipient containing vitamins beneficial to the skin:
    about 0.0075 g of 5-methoxypsoralen
    about 2 g of ethyl hexyl paramethoxy cinnamate
    about 1 of 3-(4-methylbenzylidene)-Camphor.

5. A product according to claim 1 which comprises between about 5 and about 20 mmg. of 5-methoxypsoralen per 100 grams of said product.

6. The sun tanning product of claim 1 wherein the total quantity of said 5-methoxypsoralen comprises:
    from about 0.6 to about 3 percent by weight of said product of bergamot oil, said oil containing from about 1 to 5 parts per thousand by weight of said 5-methoxypsoralen, and
    relatively pure 5-methoxypsoralen.

7. A sun tanning product according to claim 6 further comprising from about 0.6 to about 2.0 percent by weight of said product of bergamot oil.

8. A sun tanning product according to claim 6 further comprising from about 1.0 to about 2.0 percent by weight of said product of bergamot oil.

9. A sun tanning product according to claim 1 comprising per 100 g of product in oily excipient:
    about 3 g of about 4% pure bergamot essence, to total about 0.012 g bergaptene,
    about 0.003 g of pure bergaptene,
    about 3 g of ethyl hexyl paramethoxy cinnamate; and
    about 1 g of 3-(4-methylbenzylidene)-Camphor.

* * * * *